(12) United States Patent
Becton et al.

(10) Patent No.: US 7,230,163 B2
(45) Date of Patent: Jun. 12, 2007

(54) METHOD OF IMPROVING CROP YIELDS

(75) Inventors: Abner James Becton, Idalou, TX (US); Leo Neal Namken, Weslaco, TX (US)

(73) Assignee: United Agri Products, Greeley, CO (US)

(*) Notice: Subject to any disclaimer, the term of this patent is extended or adjusted under 35 U.S.C. 154(b) by 237 days.

(21) Appl. No.: 10/976,016

(22) Filed: Oct. 27, 2004

(65) Prior Publication Data

US 2006/0030488 A1 Feb. 9, 2006

Related U.S. Application Data

(63) Continuation of application No. 10/268,621, filed on Oct. 9, 2002, now abandoned.

(51) Int. Cl.
*C12N 15/82* (2006.01)
*A01H 3/04* (2006.01)

(52) U.S. Cl. ............... 800/288; 800/290; 800/300

(58) Field of Classification Search ............ None
See application file for complete search history.

(56) References Cited

U.S. PATENT DOCUMENTS

| | | | |
|---|---|---|---|
| 5,004,863 A | | 4/1991 | Umbeck |
| 5,608,147 A | * | 3/1997 | Kaphammer ............ 800/294 |
| 6,361,999 B1 | | 3/2002 | Lin et al. |
| 6,479,287 B1 | | 11/2002 | Reichert et al. |
| 6,489,541 B1 | | 12/2002 | Bandurski et al. |
| 6,528,703 B1 | | 3/2003 | Chou |

OTHER PUBLICATIONS

Duggleby 1997, Gene 190:245-249.*

* cited by examiner

*Primary Examiner*—David H Kruse
(74) *Attorney, Agent, or Firm*—Sheridan Ross P.C.

(57) ABSTRACT

The invention provides a method of improving the yield of a crop. The method comprises growing transgenic plants to produce a crop, the transgenic plants being able to metabolize at least one synthetic auxin. A synthetic auxin is applied to the plants at least once during their growth, the synthetic auxin being one that can be metabolized by the transgenic plants. Finally, the crop is harvested.

13 Claims, 2 Drawing Sheets

SEQUENCE LISTING

<160> NUMBER OF SEQ ID NOS: 3

<210> SEQ ID NO 1
<211> LENGTH: 287
<212> TYPE: PRT
<213> ORGANISM: Alcaligenes eutrophus

<400> SEQUENCE: 1

```
Met Ser Val Val Ala Asn Pro Leu His Pro Leu Phe Ala Ala Gly Val
1               5                   10                  15

Glu Asp Ile Asp Leu Arg Glu Ala Leu Gly Ser Thr Glu Val Arg Glu
            20                  25                  30

Ile Glu Arg Leu Met Asp Glu Lys Ser Val Leu Val Phe Arg Gly Gln
        35                  40                  45

Pro Leu Ser Gln Asp Gln Gln Ile Ala Phe Ala Arg Asn Phe Gly Pro
    50                  55                  60

Leu Glu Gly Gly Phe Ile Lys Val Asn Gln Arg Pro Ser Arg Phe Lys
65                  70                  75                  80

Tyr Ala Glu Leu Ala Asp Ile Ser Asn Val Ser Leu Asp Gly Lys Val
                85                  90                  95

Ala Gln Arg Asp Ala Arg Glu Val Val Gly Asn Phe Ala Asn Gln Leu
            100                 105                 110

Trp His Ser Asp Ser Ser Phe Gln Gln Pro Ala Ala Arg Tyr Ser Met
        115                 120                 125

Leu Ser Ala Val Val Val Pro Pro Ser Gly Gly Asp Thr Glu Phe Cys
    130                 135                 140

Asp Met Arg Ala Ala Tyr Asp Ala Leu Pro Arg Asp Leu Gln Ser Glu
145                 150                 155                 160

Leu Glu Gly Leu Arg Ala Glu His Tyr Ala Leu Asn Ser Arg Phe Leu
                165                 170                 175

Leu Gly Asp Thr Asp Tyr Ser Glu Ala Gln Arg Asn Ala Met Pro Pro
            180                 185                 190
```

```
Val Asn Trp Pro Leu Val Arg Thr His Ala Gly Ser Gly Arg Lys Phe
        195                 200                 205

Leu Phe Ile Gly Ala His Ala Ser His Val Glu Gly Leu Pro Val Ala
        210                 215                 220

Glu Gly Arg Met Leu Leu Ala Glu Leu Leu His Ala Thr Gln Arg
225                 230                 235                 240

Glu Phe Val Tyr Arg His Arg Trp Asn Val Gly Asp Leu Val Met Trp
                245                 250                 255

Asp Asn Arg Cys Val Leu His Arg Gly Arg Arg Tyr Asp Ile Ser Ala
                260                 265                 270

Arg Arg Glu Leu Arg Arg Ala Thr Thr Leu Asp Asp Ala Val Val
        275                 280                 285

<210> SEQ ID NO 2
<211> LENGTH: 864
<212> TYPE: DNA
<213> ORGANISM: Artificial sequence
<220> FEATURE:
<223> OTHER INFORMATION: Dicot ORF for degradation of 2,4-D
<220> FEATURE:
<221> NAME/KEY: exon
<222> LOCATION: (1)..(864)
<223> OTHER INFORMATION:

<400> SEQUENCE: 2 atg tct gtt gtt gct aac cct ttg cat cct ttg ttc gct gct gga gtt       48
Met Ser Val Val Ala Asn Pro Leu His Pro Leu Phe Ala Ala Gly Val
1               5                  10                  15 gag gat att gat ctc aga gaa gca ttg ggt tct act gag gtg aga gaa       96
Glu Asp Ile Asp Leu Arg Glu Ala Leu Gly Ser Thr Glu Val Arg Glu
            20                  25                  30 att gag aga ctc atg gac gaa aag tca gtt ctc gtt ttc aga ggt caa      144
Ile Glu Arg Leu Met Asp Glu Lys Ser Val Leu Val Phe Arg Gly Gln
        35                  40                  45 cca ctc tca cag gat caa cag att gct ttt gct agg aat ttt gga cct      192
Pro Leu Ser Gln Asp Gln Gln Ile Ala Phe Ala Arg Asn Phe Gly Pro
    50                  55                  60 ttg gag ggt gga ttc atc aaa gtg aac cag aga cca tct agg ttc aaa      240
Leu Glu Gly Gly Phe Ile Lys Val Asn Gln Arg Pro Ser Arg Phe Lys
65                  70                  75                  80 tat gct gaa ctc gct gat atc tct aat gtt tca ttg gat ggt aag gtg      288
Tyr Ala Glu Leu Ala Asp Ile Ser Asn Val Ser Leu Asp Gly Lys Val
                85                  90                  95 gca caa aga gac gct aga gaa gtt gtg gga aat ttt gca aat caa ttg      336
Ala Gln Arg Asp Ala Arg Glu Val Val Gly Asn Phe Ala Asn Gln Leu
            100                 105                 110 tgg cat tct gat tct tca ttc caa cag cca gca gct aga tat tct atg      384
Trp His Ser Asp Ser Ser Phe Gln Gln Pro Ala Ala Arg Tyr Ser Met
        115                 120                 125 ttg tca gct gtt gtt gtg cct cct tct gga ggt gat aca gaa ttt tgt      432
Leu Ser Ala Val Val Val Pro Pro Ser Gly Gly Asp Thr Glu Phe Cys
    130                 135                 140 gat atg agg gca gct tac gat gct ctc cca agg gat ttg cag tct gaa      480
Asp Met Arg Ala Ala Tyr Asp Ala Leu Pro Arg Asp Leu Gln Ser Glu
145                 150                 155                 160 ctc gag gga ttg aga gct gaa cat tac gct ttg aac tca aga ttt ctc      528
Leu Glu Gly Leu Arg Ala Glu His Tyr Ala Leu Asn Ser Arg Phe Leu
                165                 170                 175 ttg gga gat act gat tac tca gag gca cag aga aac gct atg cct cct      576
Leu Gly Asp Thr Asp Tyr Ser Glu Ala Gln Arg Asn Ala Met Pro Pro
            180                 185                 190
```

| | |
|---|---|
| gtt aac tgg cct ctc gtt agg act cat gct ggt tct ggt aga aag ttc<br>Val Asn Trp Pro Leu Val Arg Thr His Ala Gly Ser Gly Arg Lys Phe<br>      195                       200               205 | 624 |
| ttg ttt att gga gca cat gct tca cat gtt gag ggt ctc cct gtt gct<br>Leu Phe Ile Gly Ala His Ala Ser His Val Glu Gly Leu Pro Val Ala<br> 210                       215                   220 | 672 |
| gag gga aga atg ttg ctc gct gaa ttg ctc gaa cat gct act caa aga<br>Glu Gly Arg Met Leu Leu Ala Glu Leu Leu Glu His Ala Thr Gln Arg<br>225                   230                   235               240 | 720 |
| gag ttt gtt tat aga cac aga tgg aat gtt ggt gac ttg gtt atg tgg<br>Glu Phe Val Tyr Arg His Arg Trp Asn Val Gly Asp Leu Val Met Trp<br>               245                   250               255 | 768 |
| gat aat aga tgt gtg ttg cat aga ggt agg aga tat gat att tct gct<br>Asp Asn Arg Cys Val Leu His Arg Gly Arg Arg Tyr Asp Ile Ser Ala<br>         260                     265                   270 | 816 |
| aga agg gaa ctc aga agg gct act act ttg gat gac gct gtt gtt tag<br>Arg Arg Glu Leu Arg Arg Ala Thr Thr Leu Asp Asp Ala Val Val<br>               275                     280               285 | 864 |

<210> SEQ ID NO 3
<211> LENGTH: 918
<212> TYPE: DNA
<213> ORGANISM: Artificial sequence
<220> FEATURE:
<223> OTHER INFORMATION: Dicot gene for degradation of 2,4-D
<220> FEATURE:
<221> NAME/KEY: exon
<222> LOCATION: (45)..(908)
<223> OTHER INFORMATION:

<400> SEQUENCE: 3

| | |
|---|---|
| agatcctttt tatttttaat tttctttcaa atacttccag atcc atg tct gtt gtt<br>                                                                            Met Ser Val Val<br>                                                                                       1 | 56 |
| gct aac cct ttg cat cct ttg ttc gct gct gga gtt gag gat att gat<br>Ala Asn Pro Leu His Pro Leu Phe Ala Ala Gly Val Glu Asp Ile Asp<br>5                   10                      15                     20 | 104 |
| ctc aga gaa gca ttg ggt tct act gag gtg aga gaa att gag aga ctc<br>Leu Arg Glu Ala Leu Gly Ser Thr Glu Val Arg Glu Ile Glu Arg Leu<br>                  25                      30                     35 | 152 |
| atg gac gaa aag tca gtt ctc gtt ttc aga ggt caa cca ctc tca cag<br>Met Asp Glu Lys Ser Val Leu Val Phe Arg Gly Gln Pro Leu Ser Gln<br>                40                      45                     50 | 200 |
| gat caa cag att gct ttt gct agg aat ttt gga cct ttg gag ggt gga<br>Asp Gln Gln Ile Ala Phe Ala Arg Asn Phe Gly Pro Leu Glu Gly Gly<br>                  55                      60                     65 | 248 |
| ttc atc aaa gtg aac cag aga cca tct agg ttc aaa tat gct gaa ctc<br>Phe Ile Lys Val Asn Gln Arg Pro Ser Arg Phe Lys Tyr Ala Glu Leu<br>70                   75                      80 | 296 |
| gct gat atc tct aat gtt tca ttg gat ggt aag gtg gca caa aga gac<br>Ala Asp Ile Ser Asn Val Ser Leu Asp Gly Lys Val Ala Gln Arg Asp<br>85                   90                      95                   100 | 344 |
| gct aga gaa gtt gtg gga aat ttt gca aat caa ttg tgg cat tct gat<br>Ala Arg Glu Val Val Gly Asn Phe Ala Asn Gln Leu Trp His Ser Asp<br>                 105                     110                  115 | 392 |
| tct tca ttc caa cag cca gca gct aga tat tct atg ttg tca gct gtt<br>Ser Ser Phe Gln Gln Pro Ala Ala Arg Tyr Ser Met Leu Ser Ala Val<br>               120                     125                     130 | 440 |
| gtt gtg cct cct tct gga ggt gat aca gaa ttt tgt gat atg agg gca<br>Val Val Pro Pro Ser Gly Gly Asp Thr Glu Phe Cys Asp Met Arg Ala<br>         135                     140                     145 | 488 |

-continued

```
gct tac gat gct ctc cca agg gat ttg cag tct gaa ctc gag gga ttg      536
Ala Tyr Asp Ala Leu Pro Arg Asp Leu Gln Ser Glu Leu Glu Gly Leu
    150                 155                 160 aga gct gaa cat tac gct ttg aac tca aga ttt ctc ttg gga gat act      584
Arg Ala Glu His Tyr Ala Leu Asn Ser Arg Phe Leu Leu Gly Asp Thr
165                 170                 175                 180 gat tac tca gag gca cag aga aac gct atg cct cct gtt aac tgg cct      632
Asp Tyr Ser Glu Ala Gln Arg Asn Ala Met Pro Pro Val Asn Trp Pro
                185                 190                 195 ctc gtt agg act cat gct ggt tct ggt aga aag ttc ttg ttt att gga      680
Leu Val Arg Thr His Ala Gly Ser Gly Arg Lys Phe Leu Phe Ile Gly
            200                 205                 210 gca cat gct tca cat gtt gag ggt ctc cct gtt gct gag gga aga atg      728
Ala His Ala Ser His Val Glu Gly Leu Pro Val Ala Glu Gly Arg Met
        215                 220                 225 ttg ctc gct gaa ttg ctc gaa cat gct act caa aga gag ttt gtt tat      776
Leu Leu Ala Glu Leu Leu Glu His Ala Thr Gln Arg Glu Phe Val Tyr
    230                 235                 240 aga cac aga tgg aat gtt ggt gac ttg gtt atg tgg gat aat aga tgt      824
Arg His Arg Trp Asn Val Gly Asp Leu Val Met Trp Asp Asn Arg Cys
245                 250                 255                 260 gtg ttg cat aga ggt agg aga tat gat att tct gct aga agg gaa ctc      872
Val Leu His Arg Gly Arg Arg Tyr Asp Ile Ser Ala Arg Arg Glu Leu
                265                 270                 275 aga agg gct act act ttg gat gac gct gtt gtt tag tgtgctggag           918
Arg Arg Ala Thr Thr Leu Asp Asp Ala Val Val
            280                 285
```

METHOD OF IMPROVING CROP YIELDS

CROSS-REFERENCE TO RELATED APPLICATIONS

The present application is a continuation of U.S. patent application Ser. No. 10/268,621, filed Oct. 9, 2002, entitled "METHOD OF IMPROVING CROP YIELDS," now abandoned, the entire disclosure of which application is considered to be part of the disclosure of the accompanying application and is hereby incorporated by reference.

FIELD OF THE INVENTION

The present invention relates to increasing crop yields. In particular, the present invention relates to increasing crop yields by applying an auxin herbicide to transgenic plants capable of metabolizing the applied auxin herbicide.

BACKGROUND OF THE INVENTION 2,4-Dichlorophenoxyacetic acid (2,4-D) is a herbicide used primarily to control dicotyledonous weeds. 2,4-D is broken down in soil by a variety of microorganisms, including *Alcaligenes eutrophus*. A gene (tfdA) has been isolated from strains of *A. eutrophus* which encodes the first enzyme in the 2,4-D degradation pathway of these bacteria. This enzyme is a dioxygenase which catalyzes the conversion of 2,4-D to 2,4-dichlorophenol (DCP).

Transgenic tobacco plants, cotton plants, and hardwood trees containing the tfdA gene have been reported to have increased tolerance to 2,4-D. Streber et al., *Bio/Technology*, 7, 811-816 (1989); Lyon et al., *Plant Molec. Biol.*, 13, 533-540 (1989); Bayley et al., *Theor. Appl. Genet.*, 83, 645-649 (1992); Llewellyn and Last, in *Herbicide-Resistant Crops* Chapter 10, pages 159-174 (Duke, ed., CRC Lewis Publishers 1996); Last and Llewellyn, *Weed Science*, 47, 401-404 (1999); U.S. Pat. Nos. 5,608,147, 6,100,446, and 6,153,401; PCT application WO 95/18862. However, 2,4-D-tolerant transgenic cotton has been reported to have significantly reduced growth rates when sprayed with 2,4-D at levels that might be encountered in agricultural situations. Last and Llewellyn, *Weed Science*, 47, 401-404 (1999).

Increases in growth and yields have been reported to occur from applications of sublethal concentrations of 2,4-D and other herbicides to plants sensitive to them. See, Allender, *J. Plant Nutrition.*, 20,69-80 (1997); Moffett et al., *Crop Sci.*, 20,747-750 (1980); Wiedman and Appleby, *Weed Res.*, 12, 65-74 (1972); Miller et al., *Crop Sci.*, 2, 114-116 (1962); McIlrath and Ergle, *Botanical Gazette*, 461-467 (1953); McIlrath and Ergle, *Plant Physiol.*, 693-702 (1952). However, the growth stimulation is usually small, highly variable, transitory, and difficult to reproduce in the field. Allender et al., *J. Plant Nutrition.*, 20, 81-95 (1997).

SUMMARY OF THE INVENTION

The invention provides a method of improving the yield of a crop. The method comprises growing transgenic plants to produce a crop, the transgenic plants being able to metabolize at least one synthetic auxin. A synthetic auxin is applied to the plants at least once during their growth, the synthetic auxin being one that can be metabolized by the transgenic plants. Finally, the crop is harvested.

Figure 1:
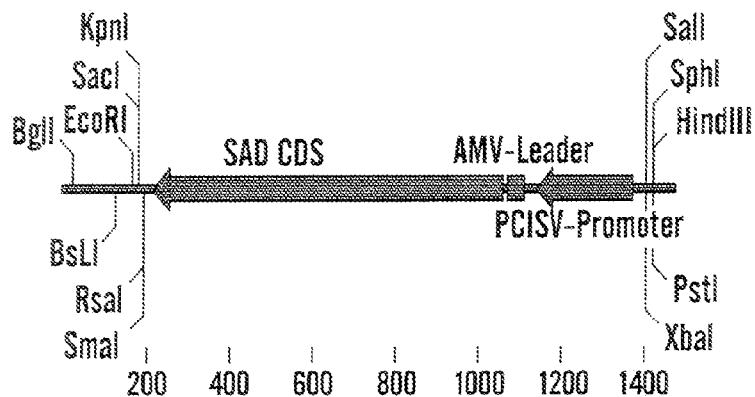
FIG. 1: Diagram of pProPClSV-SAD.

In these figures, SAD=2,4-D-degrading synthetic gene adapted for dicots; CDS=coding sequence; AMV-Leader=5' untranslated leader sequence from the 35S transcript of alfalfa mosaic virus; PClSV-Promoter=peanut chlorotic streak virus promoter; T-Left=T-DNA left border from *Agrobacterium tumefaciens* nopaline Ti plasmid pTiT37; 35SPolyA=3' polyadenylation (polyA) termination signal sequence from the cauliflower mosaic virus (CaMV) 35S transcript; NPTII=neomycin phosphotransferase II; g7PolyA=3' polyA termination signal from gene 7 within the T-Left border of an *A. tumefaciens* octopine plasmid; MCS=multiple cloning site; T-Right=T-DNA right border from *A. tumefaciens* Ti plasmid pTiT37.

DETAILED DESCRIPTION OF THE PRESENTLY-PREFERRED EMBODIMENTS OF THE INVENTION

"Synthetic auxins" are compounds generally used as herbicides. Thus, they are also referred to as "auxin herbicides." Preferred synthetic auxins (auxin herbicides) for use in the present invention are the phenoxy auxins (phenoxy herbicides), which include 4-chlorophenoxyacetic acid (4-CPA), 2,4-dichlorophenoxyacetic acid (2,4-D), 2-methyl-4-chlorophenoxyacetic acid (MCPA), 2,4,5-trichlorophenoxyacetic acid (2,4,5-T), 2,4-dichlorophenoxybutyric acid (2,4-DB), 4-(2-methyl-4-chlorophenoxy)butyric acid, 2-(4-chlorophenoxy)propionic acid, 2-(2,4-dichlorophenoxy)propionic acid, 2-(2,4,5-trichlorophenoxy)propionic acid, and salts and esters of these acids. Most preferred are 2,4-D, 2,4-DB, and esters thereof. Auxin herbicides, including phenoxy herbicides, are available commercially. See *Crop Protection Reference* (Chemical & Pharmaceutical Press, Inc., New York, N.Y., 11th ed., 1995).

A transgenic plant according to the invention is a plant which is tolerant to at least one synthetic auxin to which the corresponding nontransgenic plant is sensitive. "Tolerant" means that the transgenic plant can grow in the presence of an amount of an auxin herbicide which inhibits the growth of the corresponding nontransgenic plant and/or that the transgenic plant is not injured by an amount of auxin herbicide which injures the nontransgenic plant. "Sensitive" means that the nontransgenic plant is injured or killed by one or more auxin herbicides. In particular, nontransgenic dicotyledonous plants are severely injured or killed by auxin herbicides. Nontransgenic monocotyledonous plants are much less sensitive to auxin herbicides than dicotyledonous plants, but monocotyledonous plants can be injured by auxin herbicides applied to them at particular developmental stages (e.g., grain fill) or during times of stress. The transgenic plants of the invention are tolerant because they are able to metabolize one or more synthetic auxins as a result of the expression of heterologous DNA coding for one or more enzymes which metabolize the synthetic auxin(s) so that the synthetic auxin(s) are no longer harmful to plants. "Heterologous DNA" is used herein to mean DNA not found in the plant, such as DNA from a microorganism or another species or strain of plant.

To prepare the transgenic plants of the invention, a DNA molecule comprising DNA coding for an enzyme or enzymes which metabolize(s) at least one synthetic auxin is used. The DNA molecule may be a cDNA clone or a genomic clone isolated from a natural source. Methods of isolating and identifying cDNA and genomic clones from such sources are well known in the art. See, e.g., Maniatis et al., *Molecular Cloning: A Laboratory Manual* (Cold Spring Harbor, N.Y., 1982); Sambrook et al., *Molecular Cloning: A Laboratory Manual* (Cold Spring Harbor, N.Y., 1989).

The phenoxy herbicides are broken down in soil by a variety of microorganisms, including bacteria, yeasts, and fungi from several taxonomic groups. See, e.g., Llwellyn and Last, in *Herbicide-Resistant Crops*, Chapter 10 (Stephen O. Duke, ed.) (CRC Lewis Publishers, New York, N.Y., (1996)); Bayley et al., *Theor. Appl. Genet.*, 83, 645-649 (1992), Lyon et al., *Plant Molec. Biol.*, 13, 533-540 (1989); Streber et al., *J. Bacteriology*, 169,2950-2955 (1987); Han and New, *Soil Biol. Biochem.*, 26, 1689-1695 (1994); Donnelly et al., *Applied And Environmental Microbiology*, 59, 2642-2647 (1993); Loos, in *Degradation Of Herbicides*, pages 1-49 (Kearney and Kaufman, eds., Marcel Dekker, Inc., New York 1969), and references cited in these references. Specific microoganisms include strains of *Acinetobacter, Achromobacter, Alcaligenes, Arthrobacter, Corynebacterium, Flavobacterium, Pseudomonas,* and *Actinomycetes* (e.g., *Nocardia* spp. and *Streptomyces viridochromogenes*). Additional strains of bacteria, yeast and fungi that metabolize phenoxy herbicides can be obtained by methods well known in the art (e.g., by isolation from soils where the phenoxy herbicides are used or manufactured by the enrichment culture technique (see, e.g., Loos, in *Degradation Of Herbicides*, pages 1-49 (Kearney and Kaufman, eds., Marcel Dekker, Inc., New York 1969); Han and New, *Soil Biol. Biochem.*, 26, 1689-1695 (1994)).

The most well-characterized organisms are strains of *Alcaligenes eutrophus*, and it is from strains of *A. eutrophus* that the tfdA gene used to produce 2,4-D-tolerant transgenic plants was isolated. Additional cDNA and genomic clones coding for phenoxy-herbicide-metabolizing enzymes can be obtained from microorganisms that metabolize one or more phenoxy herbicides by methods well known in the art (e.g., in a manner similar to those used to isolate and identify the known tfdA clones). See, e.g., Maniatis et al., *Molecular Cloning: A Laboratory Manual*, Cold Spring Harbor, N.Y. (1982); Sambrook et al., *Molecular Cloning: A Laboratory Manual*, Cold Spring Harbor, N.Y. (1989); Streber et al., *Bio/Technology*, 7, 811-816 (1989); Streber et al., *J. Bacteriology*, 169, 2950-2955 (1987); Lyon et al., *Plant Molec. Biol.*, 13, 533-540 (1989); Bayley et al., *Theor. Appl. Genet.*, 83, 645-649 (1992); Perkins and Lurquin, *J. Bacteriology*, 170, 5669-5672 (1988); Llewellyn and Last, in *Herbicide-Resistant Crops* Chapter 10, pages 159-174 (Duke, ed., CRC Lewis Publishers 1996); Last and Llewellyn, *Weed Science*, 47,401-404 (1999); U.S. Pat. Nos. 5,608,147, 6,100,446 and 6,153,401; and PCT application WO 95/18862. In addition, isolated clones, portions of them, or sequences from them could be used as probes to identify and isolate additional clones. See, e.g., Perkins and Lurquin, *J. Bacteriology*, 170, 5669-5672 (1988); Bayley et al., *Theor. Appl. Genet.*, 83, 645-649 (1992); U.S. Pat. Nos. 6,100,446 and 6,153,401. See also Maniatis et al., *Molecular Cloning: A Laboratory Manual*, Cold Spring Harbor, N.Y. (1982), Sambrook et al., *Molecular Cloning: A Laboratory Manual*, Cold Spring Harbor, N.Y. (1989).

The DNA molecules comprising DNA encoding an enzyme or enzymes which metabolize(s) at least one synthetic auxin can also be fully or partially chemically synthesized using the sequences of isolated clones. To do so, a cDNA or genomic clone, obtained as described in the previous paragraph, is sequenced by methods well known in the art. See, e.g., Maniatis et al., *Molecular Cloning: A Laboratory Manual*, Cold Spring Harbor, N.Y. (1982), Sambrook et al., *Molecular Cloning: A Laboratory Manual*, Cold Spring Harbor, N.Y. (1989). A synthetic DNA sequence comprising the coding sequence of the cDNA or genomic clone can be fully or partially chemically synthesized using methods well known in the art. See, e.g., Maniatis et al., *Molecular Cloning: A Laboratory Manual*, Cold Spring Harbor, N.Y. (1982), Sambrook et al., *Molecular Cloning: A Laboratory Manual*, Cold Spring Harbor, N.Y. (1989). For instance, DNA sequences may be synthesized by phosphoamidite chemistry in an automated DNA synthesizer. Also, the sequence of the tfdA gene from *A. eutrophus* JMP134 is publically available (see Streber et al., *J. Bacteriology*, 169,2950-2955 (1987), U.S. Pat. Nos. 6,100,446 and 6,153, 401, and GenBank (accession number M16730)), and a synthetic DNA sequence comprising the coding sequence of the *A. eutrophus* tfdA gene can also be fully or partially chemically synthesized.

Chemical synthesis has a number of advantages. For instance, using chemical synthesis, the sequence of the DNA molecule or its encoded protein can be readily changed to, e.g., optimize expression (e.g., eliminate mRNA secondary structures that interfere with transcription or translation, eliminate undesired potential polyadenylation sequences, and alter the A+T and G+C content), add unique restriction sites at convenient points, delete protease cleavage sites, etc. In particular, chemical synthesis is desirable because codons preferred by the plant in which the DNA sequence will be expressed can be used to optimize expression. Not all of the codons need to be changed to obtain improved expression, but preferably at least the codons least preferred by the plant are changed to plant-preferred codons. "Codons least preferred by the plant" are those codons in the heterologous DNA sequence that are used least by the plant in question to encode a particular amino acid. "Plant-preferred codons" are codons which are used more frequently by a plant to encode a particular amino acid than is the codon encoding that amino acid in the heterologous DNA sequence. Preferably, the plant-preferred codon is the codon used most frequently by the plant to encode the amino acid. The plant codon usage may be that of plants in general, a class of plants (e.g., dicotyledonous plants), a specific type of plant (e.g., tobacco, soybeans, cotton or tomatoes), etc. The codon usage or preferences of a plant or plants can be deduced by methods known in the art. See, e.g., *Maximizing Gene Expression*, pages 225-85 (Reznikoff & Gold, eds., 1986), Perlak, et al., *Proc. Natl. Acad. Sci. USA*, 88, 3324-3328 (1991), PCT WO 97/31115, PCT WO 97/11086, EP 646643, EP 553494, and U.S. Pat. Nos. 5,689,052, 5,567,862, 5,567, 600, 5,552,299 and 5,017,692. For instance, the codons used by the plant or plants to encode all of the different amino acids in a selection of proteins expressed by the plant or plants, preferably those proteins which are highly expressed, are tabulated. This can be done manually or using software designed for this purpose (see PCT application WO 97/11086). Preferably, greater than about 50%, most preferably at least about 80%, of the codons of the heterologous DNA sequence are changed to plant-preferred codons.

In addition, DNA molecules comprising DNA coding for mutant enzymes that metabolize auxin herbicides can be used. Such mutant enzymes would have an amino acid sequence which is the same as that of a naturally-occurring enzyme, such as the dioxygenases produced by the *A.*

*eutrophus* tfdA clones, except that one or more amino acids is added, deleted, or substituted for the amino acids of the naturally-occurring enzyme. DNA coding for such mutant enzymes can be prepared using, for example, oligonucleotide-directed mutagenesis, linker-scanning mutagenesis, mutagenesis using the polymerase chain reaction, chemical synthesis, and the like. See Ausubel et al. (eds.), *Current Protocols In Molecular Biology* (Wiley Interscience 1990) and McPherson (ed.), *Directed Mutagenesis: A Practical Approach* (IRL Press 1991).

"DNA constructs" are defined herein to be constructed (non-naturally occurring) DNA molecules useful for introducing DNA into host cells, and the term includes chimeric genes, expression cassettes, and vectors. DNA constructs for use in the present invention comprise DNA coding for an auxin herbicide-metabolizing enzyme or enzymes operatively linked to expression control sequences.

As used herein "operatively linked" refers to the linking of DNA sequences (including the order of the sequences, the orientation of the sequences, and the relative spacing of the various sequences) in such a manner that the encoded proteins are expressed. Methods of operatively linking expression control sequences to coding sequences are well known in the art. See, e.g., Maniatis et al., *Molecular Cloning: A Laboratory Manual*, Cold Spring Harbor, N.Y. (1982), Sambrook et al., *Molecular Cloning. A Laboratory Manual*, Cold Spring Harbor, N.Y. (1989).

"Expression control sequences" are DNA sequences involved in any way in the control of transcription or translation. Suitable expression control sequences and methods of making and using them are well known in the art.

The expression control sequences must include a promoter. The promoter may be any DNA sequence which shows transcriptional activity in the chosen plant(s). The promoter may be inducible or constitutive. It may be naturally-occurring, may be composed of portions of various naturally-occurring promoters, or may be partially or totally synthetic. Guidance for the design of promoters is provided by studies of promoter structure, such as that of Harley and Reynolds, *Nucleic Acids Res.*, 15, 2343-61 (1987). Also, the location of the promoter relative to the transcription start may be optimized. See, e.g., Roberts, et al., *Proc. Natl. Acad. Sci. USA*, 76, 760-4 (1979). Many suitable promoters are well known in the art.

For instance, suitable constitutive promoters for use in plants include: the promoters from plant viruses, such as the full-length transcript promoter from peanut chlorotic streak virus (U.S. Pat. No. 5,850,019), the 35S promoter from cauliflower mosaic virus (Odell et al., *Nature* 313:810-812 (1985), promoters of Chlorella virus methyltransferase genes (U.S. Pat. No. 5,563,328), and the full-length transcript promoter from figwort mosaic virus (U.S. Pat. No. 5,378,619); the promoters from such genes as rice actin (McElroy et al., *Plant Cell* 2:163-171 (1990)), ubiquitin (Christensen et al., *Plant Mol. Biol.* 12:619-632 (1989) and Christensen et al., *Plant Mol. Biol.* 18:675-689 (1992)), pEMU (Last et al., *Theor. Appl. Genet.* 81:581-588 (1991)), MAS (Velten et al., *EMBO J.* 3:2723-2730 (1984)), maize H3 histone (Lepetit et al., *Mol. Gen. Genet.* 231:276-285 (1992) and Atanassova et al., *Plant Journal* 2(3):291-300 (1992)), *Brassica napus* ALS3 (PCT application WO 97/41228); and promoters of various *Agrobacterium* genes (see U.S. Pat. Nos. 4,771,002, 5,102,796, 5,182,200, 5,428,147).

Suitable inducible promoters for use in plants include: the promoter from the ACE1 system which responds to copper (Mett et al. *PNAS* 90:4567-4571 (1993)); the promoter of the maize In2 gene which responds to benzenesulfonamide herbicide safeners (Hershey et al., *Mol. Gen. Genetics* 227:229-237 (1991) and Gatz et al., *Mol. Gen. Genetics* 243:32-38 (1994)), and the promoter of the Tet repressor from Tn10 (Gatz et al., *Mol. Gen. Genet.* 227:229-237 (1991). A particularly preferred inducible promoter for use in plants is one that responds to an inducing agent to which plants do not normally respond. An exemplary inducible promoter of this type is the inducible promoter from a steroid hormone gene, the transcriptional activity of which is induced by a glucocorticosteroid hormone. Schena et al., *Proc. Natl. Acad. Sci. USA* 88:10421 (1991). Other inducible promoters for use in plants are described in EP 332104, PCT WO 93/21334 and PCT WO 97/06269.

Finally, promoters composed of portions of other promoters and partially or totally synthetic promoters can be used. See, e.g., Ni et al., *Plant J.*, 7:661-676 (1995) and PCT WO 95/14098 describing such promoters for use in plants.

The promoter may include, or be modified to include, one or more enhancer elements. Preferably, the promoter will include a plurality of enhancer elements. Promoters containing enhancer elements provide for higher levels of transcription as compared to promoters which do not include them. Suitable enhancer elements for use in plants include the enhancer element from the full-length transcript promoter of peanut chlorotic streak virus (U.S. Pat. No. 5,850,019), the 35S enhancer element from cauliflower mosaic virus (U.S. Pat. Nos. 5,106,739 and 5,164,316) and the enhancer element from figwort mosaic virus (Maiti et al., *Transgenic Res.*, 6, 143-156 (1997)). Other suitable enhancers for use in other cells are known. See PCT WO 96/23898 and *Enhancers And Eukaryotic Expression* (Cold Spring Harbor Press, Cold Spring Harbor, N.Y., 1983).

For efficient expression, the coding sequences are preferably also operatively linked to a 3' untranslated sequence. The 3' untranslated sequence will include a transcription termination sequence and a polyadenylation sequence. The 3' untranslated region can be obtained from the flanking regions of genes from *Agrobacterium* spp., plant viruses, plants or other eukaryotic cells. Suitable 3' untranslated sequences for use in plants include those of the cauliflower mosaic virus 35S gene, the phaseolin seed storage protein gene, the pea ribulose biphosphate carboxylase small subunit E9 gene, the soybean 7S storage protein genes, the octopine synthase gene, and the nopaline synthase gene.

A 5' untranslated sequence is also employed. The 5' untranslated sequence is the portion of an mRNA which extends from the 5' CAP site to the translation initiation codon. This region of the mRNA is necessary for translation initiation in eukaryotes and plays a role in the regulation of gene expression. Suitable 5' untranslated regions for use in plants include those of alfalfa mosaic virus, cucumber mosaic virus coat protein gene, and tobacco mosaic virus.

As noted above, the DNA construct may be a vector. The vector may contain one or more replication systems which allow it to replicate in host cells. Self-replicating vectors include plasmids, cosmids and viral vectors. Alternatively, the vector may be an integrating vector which allows the integration into the host cell's chromosome of the sequence coding for an auxin herbicide-degrading enzyme. The vector desirably also has unique restriction sites for the insertion of DNA sequences. If a vector does not have unique restriction sites, it may be modified to introduce or eliminate restriction sites to make it more suitable for further manipulations.

The DNA constructs of the invention can be used to transform any type of plant cells (see below). A genetic marker must be used for selecting transformed plant cells ("a selection marker"). Selection markers typically allow transformed cells to be recovered by negative selection (i.e., inhibiting growth of cells that do not contain the selection marker) or by screening for a product encoded by the selection marker.

The most commonly used selectable marker gene for plant transformation is the neomycin phosphotransferase II (nptII) gene, isolated from Tn5, which, when placed under the control of plant expression control sequences, confers resistance to kanamycin. Fraley et al., *Proc. Natl. Acad. Sci. USA*, 80:4803 (1983). Another commonly used selectable marker gene is the hygromycin phosphotransferase gene which confers resistance to the antibiotic hygromycin. Vanden Elzen et al., *Plant Mol. Biol.*, 5:299 (1985).

Additional selectable marker genes of bacterial origin that confer resistance to antibiotics include gentamycin acetyl transferase, streptomycin phosphotransferase, aminoglycoside-3'-adenyl transferase, and the bleomycin resistance determinant. Hayford et al., *Plant Physiol.* 86:1216 (1988), Jones et al., *Mol. Gen. Genet.* 210:86 (1987), Svab et al., *Plant Mol. Biol.* 14:197 (1990), Hille et al., *Plant Mol. Biol.* 7:171 (1986). Other selectable marker genes confer resistance to herbicides such as glyphosate, glufosinate or bromoxynil. Comai et al., *Nature* 317:741-744 (1985), Gordon-Kamm et al., *Plant Cell* 2:603-618 (1990), Hinchee et al., *Bio/Technology*, 6:915-922 (1988); Stalker et al., *J. Biol. Chem.*, 263:6310-6314 (1988), and Stalker et al., *Science* 242:419-423 (1988).

Other selectable marker genes for plant transformation are not of bacterial origin. These genes include, for example, mouse dihydrofolate reductase, plant 5-enolpyruvylshikimate-3-phosphate synthase and plant acetolactate synthase. Eichholtz et al., *Somatic Cell Mol. Genet.* 13:67 (1987), Shah et al., *Science* 233:478 (1986), Charest et al., *Plant Cell Rep.* 8:643 (1990).

Commonly used genes for screening presumptively transformed cells include β-glucuronidase (GUS), β-galactosidase, luciferase, and chloramphenicol acetyltransferase. Jefferson, R. A., *Plant Mol. Biol. Rep.* 5:387 (1987), Teeri et al., *EMBO J.* 8:343 (1989), Koncz et al., *Proc. Natl. Acad. Sci. USA* 84:131 (1987), De Block et al., *EMBO J.* 3:1681 (1984), green fluorescent protein (GFP) (Chalfie et al., *Science* 263:802 (1994), Haseloff et al., *TIG* 11:328-329 (1995) and PCT application WO 97/41228). Another approach to the identification of relatively rare transformation events has been use of a gene that encodes a dominant constitutive regulator of the *Zea mays* anthocyanin pigmentation pathway. Ludwig et al., *Science* 247:449 (1990).

Selection based on auxin herbicide tolerance or auxin herbicide metabolism can be used in the production of auxin herbicide-tolerant plants, in which case the use of another selection marker may not be necessary. The preferred auxin herbicides are 2,4-D and its salts (including amine salts) and esters. "Tolerance" in this context means that transformed plant cells are able to grow (survive, proliferate and regenerate into plants) when placed in culture medium containing a level of the auxin herbicide that prevents untransformed cells from doing so. "Tolerance" also means that transformed plants are able to grow after application of an amount of an auxin herbicide that inhibits the growth of untransformed plants.

Methods of selecting transformed plant cells are well known in the art. Briefly, at least some of the plant cells in a population of plant cells (e.g., an explant or an embryonic suspension culture) are transformed with a DNA construct according to the invention providing for auxin herbicide metabolism (see below for transformation methods). The resulting population of plant cells is placed in culture medium containing the auxin herbicide at a concentration selected so that transformed plant cells will grow, whereas untransformed plant cells will not. Suitable concentrations of auxin herbicide can be determined empirically as is known in the art. See, e.g., U.S. Pat. No. 5,608,147. See also the Examples below. At least in the case of 2,4-D, this amount may further need to be an amount which inhibits adventitious shoot formation from untransformed plant cells and allows adventitious shoot formation from transformed plant cells. See U.S. Pat. No. 5,608,147 and PCT application WO 95/18862. In general, 2,4-D should be present in an amount ranging from about 0.001 mg/l to about 5 mg/l culture medium, preferably from about 0.01 mg/l to 0.2 mg/l culture medium.

Methods of selecting transformed plants are also known in the art. Briefly, an auxin herbicide is applied to a population of plants which may comprise one or more transgenic plants comprising a DNA construct according to the invention providing for auxin herbicide metabolism. The amount of auxin herbicide is selected so that transformed plants will grow, and the growth of untransformed plants will be inhibited. The level of inhibition must be sufficient so that transformed and untransformed plants can be readily distinguished (i.e., inhibition must be statistically significant). Such amounts can be determined empirically as is known in the art. See also *Crop Protection Reference* (Chemical & Pharmaceutical Press, Inc., New York, N.Y., 11$^{th}$ ed., 1995) and the Examples below.

The DNA constructs of the invention can be used to transform a variety of plant cells (see below). The synthetic DNA sequence coding for the auxin herbicide-metabolizing enzyme and the selection marker, if a separate selection marker is used, may be on the same or different DNA constructs. Preferably, they are arranged on a single DNA construct as a transcription unit so that all of the coding sequences are expressed together.

Suitable host cells include plant cells of any kind (see below). Preferably, the plant cell is one that does not normally metabolize auxin herbicides. However, the present invention can also be used to increase the level of metabolism of auxin herbicides in plants that normally metabolize such herbicides.

Methods of transforming plants are well known in the art and include biological and physical transformation protocols. See, for example, Miki et al., "Procedures for Introducing Foreign DNA into Plants" in *Methods in Plant Molecular Biology and Biotechnology*, Glick, B. R. and Thompson, J. E. Eds. (CRC Press, Inc., Boca Raton, 1993) pp. 67-88. In addition, vectors and in vitro culture methods for plant cell or tissue transformation and regeneration of plants are available. See, for example, Gruber et al., "Vectors for Plant Transformation" in *Methods in Plant Molecular Biology and Biotechnology*, Glick, B. R. and Thompson, J. E. Eds. (CRC Press, Inc., Boca Raton, 1993) pp. 89-119.

The most widely utilized method for introducing an expression vector into plants is based on the natural transformation system of *Agrobacterium*. See, for example, Horsch et al., *Science* 227:1229 (1985). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., *Crit. Rev. Plant. Sci.* 10:1 (1991). Descriptions of *Agrobacterium* vector systems and methods for *Agrobacterium*-mediated gene transfer are provided by numerous references. See, for example, Horsch et al., *Sci-* ence 227:1229 (1985), Hoekema et al., *Nature* 303:179 (1983), de Framond et al., *Bio/Technology* 1:262 (1983), Jordan et al., *Plant Cell Reports* 7:281-284 (1988), Leple et al., *Plant Cell Reports* 11:137-141 (1992), Stomp et al., *Plant Physiol.* 92:1226-1232 (1990), Knauf et al., *Plasmid* 8:45-54 (1982)), Gruber et al., supra, Miki et al., supra, Moloney et al., *Plant Cell Reports* 8:238 (1989), PCT applications WO84/02913, WO84/02919 and WO84/02920, EP 116,718, and U.S. Pat. Nos. 4,940,838, 5,464,763, and 5,929,300.

A generally applicable method of plant transformation is microprojectile-mediated transformation wherein DNA is carried on the surface of microprojectiles. The expression vector is introduced into plant tissues with a biolistic device that accelerates the microprojectiles to speeds sufficient to penetrate plant cell walls and membranes. Sanford et al., *Part. Sci. Technol.* 5:27 (1987), Sanford, J. C., *Trends Biotech.* 6:299 (1988), Sanford, J. C., *Physiol. Plant* 79:206 (1990), Klein et al., *Biotechnology* 10:268 (1992); Klein et al., *Nature*, 327:70-73 (1987).

Another method for physical delivery of DNA to plants is sonication of target cells. Zhang et al., *Bio/Technology* 9:996 (1991). Alternatively, liposome or spheroplast fusion have been used to introduce expression vectors into plants. Deshayes et al., *EMBO J.*, 4:2731 (1985), Christou et al., *Proc Natl. Acad. Sci. USA* 84:3962 (1987). Direct uptake of DNA into protoplasts using $CaCl_2$ precipitation, polyvinyl alcohol or poly-L-ornithine have also been reported. Hain et al., *Mol. Gen. Genet.* 199:161 (1985) and Draper et al., *Plant Cell Physiol.* 23:451 (1982). Electroporation of protoplasts and whole cells and tissues has also been described. Donn et al., In Abstracts of VIIth International Congress on Plant Cell and Tissue Culture IAPTC, A2-38, p. 53 (1990); D'Halluin et al., *Plant Cell* 4:1495-1505 (1992), Spencer et al., *Plant Mol. Biol.* 24:51-61 (1994), and Fromm et al., *Proc. Natl. Acad. Sci. USA* 82:5824 (1985). Other techniques include microinjection (Crossway, *Mol Gen. Genetics*, 202:179-185 (1985)), polyethylene glycol transformation (Krens et al., *Nature* 296:72-74 (1982)), fusion of protoplasts with other entities, either minicells, cells, lysosomes, or other fusible lipid-surfaced bodies (Fraley et al., *Proc. Natl. Acad. Sci. USA* 79:1859-1863 (1982)), and techniques set forth in U.S. Pat. No. 5,231,019.

After selection, transformed plant cells are regenerated into transgenic plants. Plant regeneration techniques are well known in the art and include those set forth in the *Handbook of Plant Cell Culture*, Volumes 1-3, Evans et al., eds. Macmillan Publishing Co., New York, N.Y. (1983, 1984, 1984, respectively); Predieri and Malavasi, *Plant Cell, Tissue, and Organ Culture* 17:133-142 (1989); James, D. J., et al., *J. Plant Physiol.* 132:148-154 (1988); Fasolo, F., et al., *Plant Cell, Tissue, and Organ Culture* 16:75-87 (1989); Valobra and James, *Plant Cell, Tissue, and Organ Culture* 21:51-54 (1990); Srivastava, P. S., et al., *Plant Science* 42:209-214 (1985); Rowland and Ogden, *Hort. Science* 27:1127-1129 (1992); Park and Son, *Plant Cell, Tissue, and Organ Culture* 15:95-105 (1988); Noh and Minocha, *Plant Cell Reports* 5:464-467 (1986); Brand and Lineberger, *Plant Science* 57:173-179 (1988); Bozhkov, P. V. et al., *Plant Cell Reports* 11:386-389 (1992); Kvaalen and von Arnold, *Plant Cell, Tissue, and Organ Culture* 27:49-57 (1991); Tremblay and Tremblay, *Plant Cell Tissue, and Organ Culture* 27:95-103 (1991); Gupta and Pullman, U.S. Pat. No. 5,036,007; Michler and Bauer, *Plant Science* 77:111-118 (1991); Wetzstein, H. Y., et al., *Plant Science* 64:193-201 (1989); McGranahan, G. H., et al., *Bio/Technology* 6:800-804 (1988); Gingas, V. M., *Hort. Science* 26:1217-1218 (1991); Chalupa, V., *Plant Cell Reports* 9:398-401 (1990); Gingas and Lineberger, *Plant Cell, Tissue, and Organ Culture* 17:191-203 (1989); Bureno, M. A., et al., *Phys. Plant.* 85:30-34 (1992); and Roberts, D. R., et al., *Can. J. Bot.* 68:1086-1090 (1990), and U.S. Pat. No. 5,608,147.

Transgenic auxin herbicide-tolerant plants of any type may be produced. In particular, dicotyledonous crop plants, including beans, soybeans, cotton, peas, potatoes, sunflowers, tomatoes, tobacco, and fruit trees, that are currently known to be injured or killed by auxin herbicides, can be transformed so that they become tolerant to these herbicides and produce greater yields of their crops. Monocotyledonous crop plants, such as corn, sorghum, small grains, sugarcane, asparagus, and grasses, which are less sensitive to auxin herbicides than dicotyledonous plants can also be transformed to increase their tolerance to these herbicides and to increase the yields of their crops. Most crop plants (e.g., soybeans, cotton, tobacco and tomatoes) are annuals, by which it is meant that they typically grow and produce their crops in a single growing season. Other crop plants (e.g., fruit trees and grasses) are perennials, by which is it meant that the plants grow and produce crops for more than a single growing season, generally several years.

To obtain an increased yield of a crop, transgenic crop plants tolerant to at least one auxin herbicide are grown in the normal manner to produce the crop. During the growth of the crop, an effective amount of an auxin herbicide to which the transgenic plants are tolerant is applied to the transgenic plants. The auxin herbicides are applied by methods well known in the art (see *Crop Protection Reference* (Chemical & Pharmaceutical Press, Inc., New York, N.Y., 11th ed., 1995)). The timing of the application(s) of the herbicide, the number of applications of the herbicide per growing season, and adequate and optimal amounts of the herbicide to be applied can be determined empirically, and doing so is within the skill in the art. It has been found that application of the auxin herbicide at the seeding/germination stage should probably be avoided. It has also been found that auxin herbicides can be applied multiple times. It has further been found that an amount of a phenoxy herbicide up to the amounts normally applied to control dicotyledonous weeds (see *Crop Protection Reference* (Chemical & Pharmaceutical Press, Inc., New York, N.Y., 11th ed., 1995)) can be used without harm to, and with increased yields of, transgenic tobacco and tomato plants (see the Examples below). Thus, the present method can also provide for weed control during the growth of crops from which increased yields will be obtained. By "increased yield" is meant that transgenic plants to which an auxin herbicide is applied produce an increased yield of a crop as compared to non-transgenic plants of the same type treated in the same manner (i.e., having the same auxin herbicide applied the same number of times and at the same times, etc.).

In a particularly preferred embodiment of the invention, the transgenic plants comprise DNA encoding an enzyme that metabolizes 2,4-D. Preferably, the DNA encodes the dioxygenase encoded by the tfdA gene which has been isolated from strains of *A. eutrophus*. It has been found that at least the bacterial start codon of the tfdA coding sequence must be replaced by a plant-preferred codon. See, e.g., Llewellyn and Last, in *Herbicide-Resistant Crops* Chapter 10, pages 159-174 (Duke, ed., CRC Lewis Publishers 1996). Preferably, additional bacterial codons of the tfdA coding sequence are replaced by plant-preferred codons to obtain better expression of the encoded dioxygenase. Plants expressing the dioxygenase encoded by the tfdA gene have been found to be tolerant to 2,4-D; they have also been found to be tolerant to 2,4-DB and MCPA, although at lower levels of herbicide than for 2,4-D (data not shown). Plants expressing this enzyme have also been reported to be tolerant to 4-CPA, but not to be tolerant to 2,4,5-T and phenoxypropionic acid herbicides. See, e.g., Llewellyn and Last, in *Herbicide-Resistant Crops* Chapter 10, pages 159-174 (Duke, ed., CRC Lewis Publishers 1996) and U.S. Pat. Nos. 6,100,446 and 6,153,401. Most important, plants expressing the dioxygenase encoded by the tfdA gene have been found to produce improved crop yields when treated with 2,4-D.

The following examples are provided for the purpose of illustration and are not intended to limit the scope of the present invention.

EXAMPLES

Example 1

Increased Yields of Vegetative Matter by Application Of 2,4-D to Transgenic Tobacco Plants A. Experimental Design The use of exogenously supplied synthetic auxins on agronomic crops to elicit direct non-herbicidal effects, with an emphasis on the potential enhancement of yield, was assessed using genetically-engineered (GE) tobacco plant lines expressing synthetic auxin metabolizing genes. Non-GE controls were used, permitting separation of the herbicidal and biological properties of the exogenously supplied synthetic auxins. Tobacco was utilized to model dry matter yield.

The research was conducted in a single phase entailing characterization of response variables when plants were subjected to maximum (1×rate=1 pound/acre of active ingredient) and low (¼×=4 ounces/acre of active ingredient) rates of exogenously applied 2,4-dichlorophenoxyacetic acid (2,4-D). GE lines of tobacco (dark fired cultivar "KY 160") expressing a synthetic gene for auxin metabolism (SAD1 or SAD2) were used, along with non-GE lines of the same genotype as control material. Commercial tobacco production has long utilized decapitation ("topping") to initiate a predictable increase in leaf weight, thickness, and dry matter yield. This yield increase is dependent upon variables, such as genotype and fertility. By utilizing controls of the same genotype and a fixed level of fertility, significant yield variation responses should be attributable to the treatment (exogenous auxin herbicide application).

The overall experimental design was comprised of three parallel completely randomized designs with spray rate and genotype as the main factors. Three replications were performed for each treatment within each experiment. Each replication was the average measurement of six plants. The tobacco lines were allowed to advance to the 6-8 leaf stage. Upon reaching this stage, the primary meristem was removed along with lower leaves so that only 4 leaves remained. Plants were then sprayed with herbicide and permitted to grow for an additional 21 days. At the end of this period, dry matter yields for both leaf and the whole plant were measured.

Yield data recorded for tobacco were leaf dry matter, leaf number, and total dry matter. Corrected plant yield and corrected leaf yield were calculated for each replication as the leaf dry matter divided by leaf number then multiplied by the expected number of leaves (6 plants×4 leaves=24). This corrected leaf yield was then added to stem yield fraction (arrived at by subtracting actual leaf yield from total plant yield) to create a corrected total plant yield. All tobacco yield measurements were recorded in grams after a 7-day drying period in ambient air dryers.

B. Transformation of Tobacco to Produce Genetically-Engineered Lines

1. Binary Plasmids for Transformation

The binary plasmids used for transformation were provided by Dr. Mel Oliver (USDA-ARS, Lubbock, Tex.). They were prepared by Dr. Oliver and colleagues as described below. Also see co-pending application 60/335,463, filed on Oct. 24, 2001, entitled "Synthetic Herbicide Resistance Gene", the complete disclosure of which is incorporated herein by reference.

The DNA sequence of a 2,4-D dioxygenase (also often referred to as a monooxygenase) gene isolated from *Alcaligenes eutrophus* was obtained from the sequence database GenBank (accession number M16730). From this DNA sequence, the amino acid sequence of the protein coded for by the single open-reading frame (ORF) was determined [SEQ ID NO:1]. A codon usage table reflecting dicotyledonous ORFs was derived from a composite selection of random cDNA sequences from cotton, *Arabidopsis* and tobacco extracted from the GenBank database. Using the plant-specific codon usage table, the derived primary amino acid sequence of the bacterial 2,4-D dioxygenase was converted into DNA coding sequences that reflected the codon preferences of dicotyledonous plants [SEQ ID NO:2].

The synthetic plant-optimized 2,4-D dioxygenase ORF [SEQ ID NO:2] was then used to design a 2,4-D dioxygenase gene capable of efficient expression in transgenic plants. This synthetic gene was designated as SAD (Synthetic gene Adapted for Dicots). In order to generate a translatable transcript once the gene had been constructed and inserted into a plant genome, a 5' untranslated leader sequence representing the 5' untranslated leader sequence from the 35S transcript of alfalfa mosaic virus (AMV; Gallie et al., *Nucleic Acids Res.*, 15:8693-8711 (1987)) was incorporated into the design of the synthetic gene. In addition, a signature sequence, encoding Cys Ala Gly, was added to the 3' end of the synthetic coding region. Finally, for ease of cloning, the designed sequence included a HindIII-specific overhang at the 5' end and a SalI-specific overhang at the 3' end. The complete designed sequence for the synthetic portion of the SAD gene is SEQ ID NO:3.

To construct the designed synthetic portions of the SAD gene, each sequence was dissected into overlapping oligonucleotides, twelve oligonucleotides for each of the two strands resulting in a total of twenty-four oligonucleotides. The oligonucleotides were synthesized using standard phosphoramidite chemistry by Integrated DNA Technologies, Inc., Coralville, Iowa. The synthetic DNA molecules were assembled using a procedure based upon the protocol described by Sutton et al. 1995 published on the World Wide Web (www.epicentre.com) using Ampliligase™ thermostable ligase (Epicentre Technologies Inc., Madison, Wis.). Oligonucleotides were first phosphorylated using T4 polynucleotide kinase (Invitrogen Life Technologies, Carlsbad, Calif.) as mixtures of upper and lower strand oligonucleotides. Each mixture contained 10 pmoles of each oligonucleotide, 70 mM Tris/HCl pH 7.6, 10 mM $MgCl_2$, 5 mM dithiothreitol (DTT), 0.1 mM ATP, and 10 units of T4 polynucleotide kinase, for a total volume of 25 µl. Phosphorylation was achieved by incubation of the mixtures at 37° C. for 30 minutes, followed by a denaturing incubation at 70° C. for 10 minutes. To anneal and ligate the oligonucleotides, each reaction mixture was retreated at 70° C. for 10 minutes in a thermocycler and subsequently cooled to 65° C. over a 10-minute period. To each mixture, 65 µl of water, 10 µl of 10× Ampliligase buffer (Epicentre Technologies), and 2 µl of Ampliligase (5 units/µl) were added sequentially, and the temperature was reduced to 40° C. over a three hour period.

At this stage, in order to improve the efficiency of cloning, the complete synthetic DNA sequence for SAD was recovered from its annealing/ligation reactions by polymerase chain reaction (PCR) in an MJ Research Inc. (Waltham, Mass.) Model PTC-100 Thermocycler using Amplitaq Gold™ DNA polymerase under conditions supplied by the manufacturer, Perkin Elmer Life Sciences (Boston, Mass.). The PCR primers used for the recovery of each sequence were a 28mer representing the 5' end of the AMV leader sequence and a 25mer specific for the 3' end of the SAD sequence. PCR fragments corresponding to the appropriate size of 918 bp were gel purified as described in Ausubel et al., *Current Protocols In Molecular Biology* (Green/Wiley Interscience, New York, 1989) and cloned between two XcmI restriction sites in pUCR19, a modified pUC19 vector designed for rapid cloning of PCR fragments using T overhangs generated by XcmI digestion (described in O'Mahony and Oliver, *Plant Molecular Biology*, 39: 809-821 (1999)) to generate the plasmid pUCRsynSAD. Once cloned into this vector, the insert was sequenced to verify the sequence integrity of the designed synthetic portion of the SAD gene. DNA sequencing was performed by use of a dRhodamine Terminator Cycle Sequencing kit (PE Applied Biosystems, Foster City, Calif.) according to the manufacturer's instructions. Sequence reactions were analyzed using a Perkin Elmer/ABI Prism 310 automated sequencer.

For the generation of a complete and plant-competent SAD gene, the synthetic portions of the SAD gene contained in pUCRsynSAD were removed by first releasing the 5' end of the synthetic sequence by digestion with XbaI and filling in the overhang with DNA polymerase I (Klenow large fragment) followed by digestion with KpnI. This fragment was ligated into the plasmid pProPClSV, a pUC19 plasmid containing an enhanced Peanut Chlorotic Streak Virus (PClSV) promoter derived from pKLP36 (described by Maiti and Shepherd, *Biochem. Biophys. Res. Com*., 244:440-444 (1998)) by cutting first with NcoI, treating with DNA polymerase I (Klenow large fragment) to fill in the generated overhang, and subsequently cutting with KpnI. This generated the plasmid pProPClSV-SAD within which the synthetic portion of the SAD gene, including the 5' AMV leader and 3' region coding for the Cys Ala Gly signature, is directly linked to the 3' end of the PClSV promoter (FIG. 1). This plasmid served as the source for the PClSV-SAD construction for insertion into the binary vectors for final gene construction prior to introduction into *Agrobacterium* for plant transformation.

Figure 2:
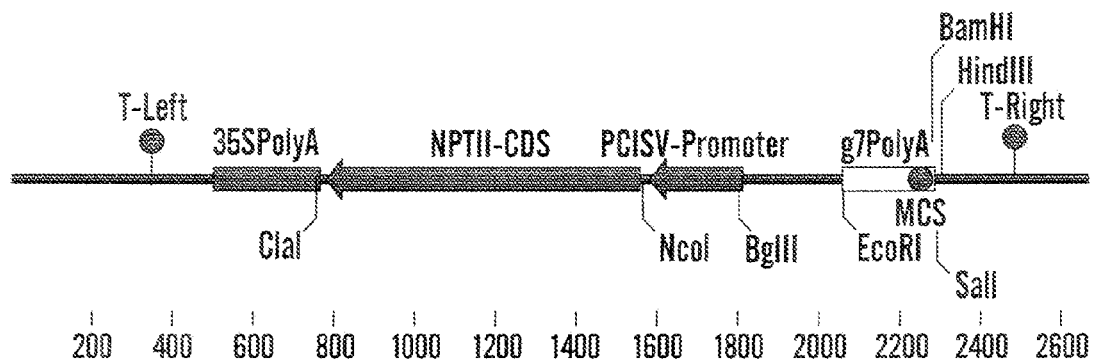
FIG. 2: Diagram of pPZP211-PNPT-311g7.
Figure 3:
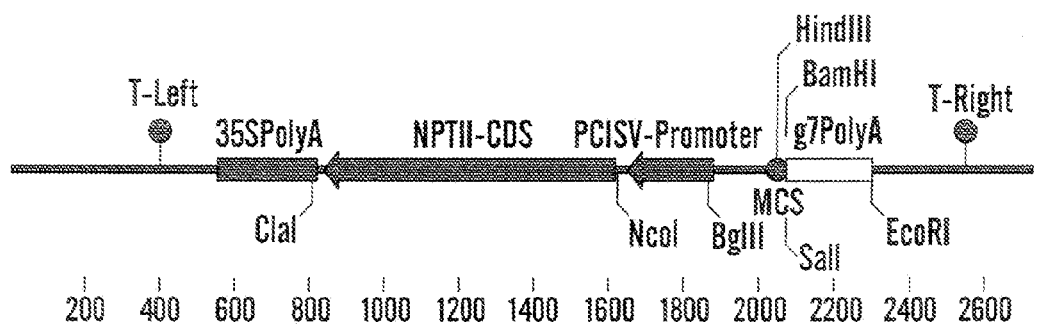
FIG. 3: Diagram of pPZP211-PNPT-512g7.
Figure 4:
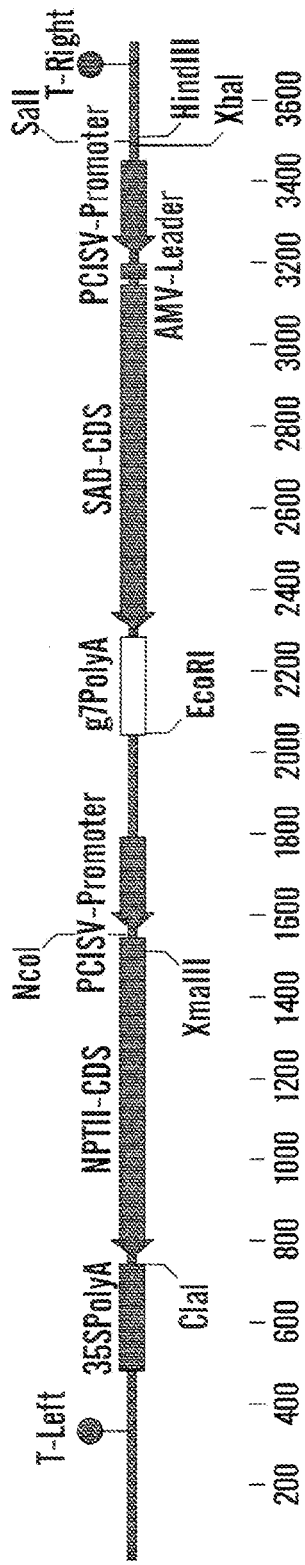
FIG. 4: Diagram of pPZP211-PNPT-311-SAD.
Figure 5:
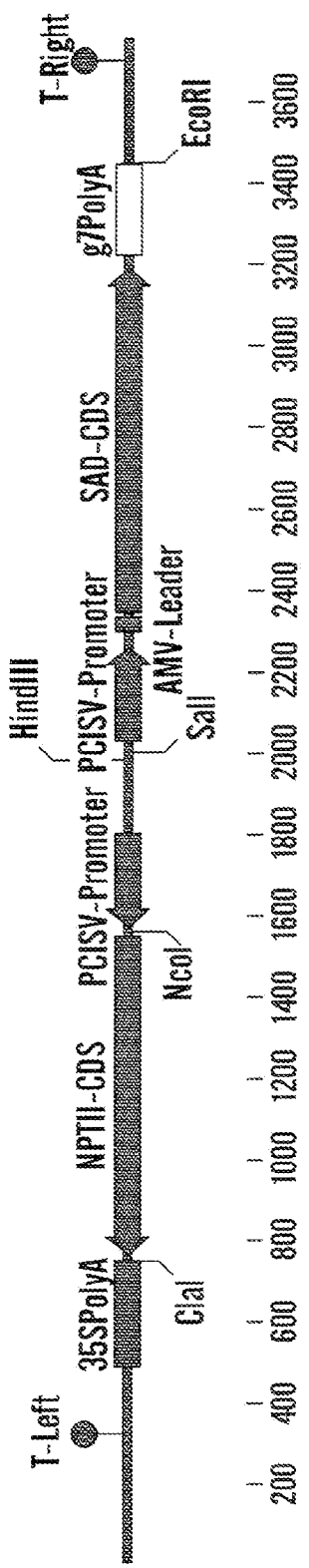
FIG. 5: Diagram of pPZP211-PNPT-512-SAD.

Two binary vectors were chosen for final SAD gene construction, pPZP211-PNPT-311 g7 (FIG. 2) and pPZP211-PNPT-512g7 (FIG. 3). These two vectors are based on the pPZP family of vectors described by Hajdukiewicz et al., *Plant Molec. Biol*., 25:989-994 (1994) and are pPZP211 derivatives in which the neomycin phosphotransferase II (NPTII) gene for kanamycin resistance is driven by the PClSV promoter and a g7 polyA termination sequence is placed adjacent to a multicloning site (MCS, FIGS. 2 and 3). The only difference between these two vectors is the position of the MCS relative to the g7 polyA termination sequence. The g7 polyA termination sequence is the 3' polyA termination signal from gene 7 within the octopine T-Left region of an octopine *Agrobacterium tumefaciens* Ti plasmid and was isolated as an EcoRI-SalI fragment from pAP2034 (Velten and Schell, *Nucleic Acids*, 13:6981-6998 (1985)).

The complete SAD gene was constructed by removal of the PClSV-SAD sequence from pProPClSV-SAD as a HindIII-SmaI fragment and insertion into both pPZP211-PNPT-311g7 and pPZP211-PNPT-512g7 that were first cut with BamHI, treated with DNA polymerase I (Klenow large fragment) to fill in the overhanging sequence, and subsequently digested with HindIII. These reactions generated the two vectors, pPZP211-PNPT-311-SAD (FIG. 4) and pPZP211-PNPT-512-SAD (FIG. 5), that contained the full plant expressible SAD gene in one of two orientations with respect to the PClSV-NPTII-35SpolyA construct. This design for insertion of the SAD gene into plant genomes was implemented because of uncertainty as to the effect of having two PClSV promoter sequences in the same plasmid on both transformation and effective transmission of the expressed trait. By putting the SAD gene in the vectors such that the PClSV promoters were inserted as both direct and inverted repeats, the possibility of a negative outcome could be avoided.

After construction, the SAD genes in each vector were sequenced as described above to ensure fidelity. This sequencing revealed that, in the construction of pProPClSV-SAD, an out-of-frame ATG codon was introduced into the 5' untranslated leader sequence. The presence of this ATG codon could alter the translatability of the transcript that would be synthesized from the SAD gene and so was deleted by PCR mutagenesis to restore the normal AMV leader sequence. Following repair, the sequence was rechecked for fidelity. The original SAD gene containing the out-of-frame ATG was labelled SAD1 (since some transformation experiments had begun using this construct). The repaired SAD gene is referred to as SAD2.

2. Transformation of Tobacco

Plasmids pPZP211-PNPT-311-SAD1 and pPZP211-PNPT-311-SAD2 were each transformed into *Agrobacterium tumefaciens* strain EHA 105 by electroporation (Dulk-Ras and Hooykaas, in *Plant Cell Electroporation and Electrofusion Protocols* (Nickloff, ed., Humana Press, Inc., Totowa, N.J.). Similar results have been obtained with plasmids pPZP211-PNPT-512-SAD1 and pPZP211-PNPT-512-SAD2 (data not shown), and they can be used in place of pPZP211-PNPT-311-SAD1 and pPZP211-PNPT-311-SAD2.

*Nicotiana tabacum* cultivar KY 160 (University of Kentucky Experiment Station) was used for all experiments. Seeds were surface sterilized and germinated on minimal medium [MS salts (Murashige and Skoog, *Physiol. Plant*, 15:473-497 (1962)); B5 vitamins (Gamborg et al., *Experimental Cell Research*, 50:151-158 (1968)), 3% sucrose, pH 5.8, solidified with 0.8% agar]. Leaves from 3-4 week old seedlings were excised, wounded with a number 11 scalpel blade, and exposed to *A. tumefacicens* carrying either pPZP211-PNPT-311-SAD1or pPZP211-PNPT-311-SAD2. After exposure to *A. tumefaciens*, explants were co-cultured on shooting medium [MS salts, B5 vitamins, 3% sucrose, 2.5 μg/l 6-benzylaminopurine, 1.0 μg/l indole-3-acetic acid, pH 5.8, solidified with 0.8% agar] overnight at 27° C. Following co-cultivation, explants were transferred to shooting medium amended with 300 mg/l kanamycin monosulfate and 500 mg/l cefatoxim. Putative transgenic shoots began to appear after 21 days, and at 30-50 days, shoots were excised and placed on minimal medium containing kanamycin monosulfate (300 mg/l) and cefatoxim (500 mg/l) for root development. Once roots were established, the plantlets were transferred into soil in the greenhouse and allowed to flower. Plants were bagged to ensure self-pollination. Seed from the T0 plants (T1 seed) was germinated on minimal medium containing 300 mg/l kanamycin monosulfate to select for kanamycin-resistant (Kan$^R$) plants. Kan$^R$ seedlings were transferred to soil for generational advance. Again, plants were bagged to ensure self-pollination. Seed from T1 plants (T2 seed) was germinated as above, and homozygous transgenic lines (lines in which all of the T2 seedlings were Kan$^R$) were selected for spray assays and yield evaluation.

C. Spray Assays

Sterile seeds of putative transgenic tobacco lines were germinated on minimal medium containing 300 mg/L kanamycin monosulfate. At 21 days post-germination, tobacco seedlings were identified as being transgenic if they both remained green and formed secondary roots. Segregating non-transgenic progeny were identified by their chlorosis, bleaching and failure to form strong root systems. Transgenic progeny (green seedlings) were transferred to 4" azalea pots filled with a 2:2:1 mix of ProMix BX (Premier Horticulture Inc., Red Hill, Pa. 18076), Masonry sand, and field soil and allowed to grow for 21 days on greenhouse benches under a 16:8 light:dark cycle. Then, the tobacco seedlings were sprayed as described below, except using a 2× rate (equivalent of 32 ounces of 2,4-D, isooctyl ester formulation, per acre) only. Ten days after spraying, the seedlings were evaluated for tolerance, Tolerance was scored as: 0=dead; 1=severe deformation symptoms; 2=mild to moderate symptoms; and 3=no symptoms.

D. Yield Assays

1. Growth Of Plants

Seed of non-transgenic tobacco lines were germinated on MS03 (MS salts, B5 vitamins, 3% sucrose) medium. Transgenic seeds were germinated on the same medium augmented with 300 mg/L kanamycin monosulfate to allow detection of any seedlings failing to carry the transgene. Thirty days after germination, seedlings were transplanted to the greenhouse into flats holding 8 trays of 6 plants each for a total of 48 plants. Plants were permitted to grow for approximately 45 days, at which time 6-8 leaves had developed. Prior to spraying, the top of the plant retaining the uppermost two leaves was removed (decapitated) resulting in the retention of 4 fully-extended leaves for each plant.

2. Spraying of Plants

For spray assays and for the yield studies, spraying was performed in an Allen Machine Works Spray Cabinet. Spray rates were established as the equivalent of 16 ounces of active ingredient per acre (1×rate), 4 ounces active ingredient/acre (¼×rate), and the control (no active ingredient per acre or 0×). The herbicide used was 2,4-D, isooctyl ester formulation (3.9 pounds of active ingredient/gallon) at equivalent rates noted above. To achieve this equivalent 1× field rate, 500 microliters of herbicide were diluted into a total volume of 50 ml. The ¼× field rate was achieved by diluting 125 microliters of herbicide in a 50 ml volume. This 50 ml was dispensed at a rate of 358.5 ml per minute in a 15" band applied by a 8001 EVS nozzle at 29 pounds per square inch (PSI). This is equivalent to 25 gallons per acre being applied at a ground speed of 1.5 MPH. Each replication was sprayed independently and permitted to dry before being moved back to the greenhouse for further growth and evaluation.

3. Determination of Dry Matter Yields

Twenty-one days after spraying, tobacco plants were harvested by cutting off all above-ground growth. The leaves were stripped off, and each plant and its leaves were bagged and dried at 75° C. with forced air for 36 hours. The plants were removed from bags, the leaves were weighed, the stems were weighed, and total plant biomass was determined as the sum of the leaf and stem weights.

4. Results

The results are presented in the following tables. Table 1 demonstrates the yield effects attributable to genotype and spray rate. This is possible because the analyses of variance (Table 2) for vegetative yield components in tobacco clearly demonstrated a genotype by spray rate interaction for all yield response variables measured, except for uncorrected plant yield. This interaction was expected, since susceptible non-transgenic control material should show a significant decrease in yield when treated with a herbicide that the control material has no tolerance to. When evaluating Table 1, note the positive yield increase in the transgenic materials. Whenever transgenic material was sprayed with either the ¼× or 1×rate of 2,4-D, a significant increase in yield was produced. This yield increase is likely a result (as noted by the leaf yield, corrected leaf yield, and percentage leaf yield responses) of increased leaf tissue and decreased stalk fraction, a highly desirable increase in any crop harvested for foliage. Additionally, non-transgenic control material is also showing this same increasing pattern across all values at the lower (¼×) application rate. This clearly shows that, at the lower evaluated ¼×rate, exogenously applied phenoxy herbicide does alter vegetative yield in a positive manner.

To summarize, vegetative data clearly demonstrated that the exogenous application of a phenoxy herbicide (in this case 2,4-D isooctyl ester) increased vegetative yield. The data further suggested that this yield increase occurred predominantly in the leaf yield component of total plant yield. This reveals a new and novel use of this herbicide, in combination with genes conditioning tolerance to it, for providing demonstrable yield increases. The commercialization of tobacco or other leaf crops expressing genes for tolerance to phenoxy herbicides would permit growers to obtain yield increases in crops normally susceptible to these same herbicides.

TABLE 1

Effect of Spray Rates of 2,4-D on Dark Fire Tobacco Genotype KY160 Means (in grams) as Conditioned by Either Herbicide Metabolic Gene

| Genotype | 2,4-D Rate[4] | Plant Yield[5] | Corrected[5] Plant Yield | Leaf Yield[5] | Corrected[5] Leaf Yield | Percent Leaf Yield[5] |
|---|---|---|---|---|---|---|
| KY 160[1] | 0 | 29.9 | 30.6 | 10.5 | 11.2 | 36.6% |
|  | 1/4X | 33.1 | 34.3 | 11.0 | 12.2 | 35.2% |
|  | 1X | 27.7 | 28.2 | 9.0 | 9.4 | 33.2% |
| SAD1[2] | 0 | 38.7 | 39.3 | 14.1 | 14.7 | 37.3% |
|  | 1/4X | 43.5 | 43.9 | 17.4 | 17.8 | 40.5% |
|  | 1X | 42.5 | 42.7 | 18.8 | 19.1 | 44.7% |
| SAD2[3] | 0 | 40.6 | 42.4 | 14.2 | 16.0 | 37.5% |
|  | 1/4X | 43.9 | 45.2 | 17.8 | 19.1 | 42.2% |
|  | 1X | 48.8 | 51.0 | 19.4 | 21.6 | 42.2% |

[1]KY-160 - Commonly grown cultivar of dark fired tobacco in Kentucky and Tennessee
[2]SAD1 - Cultivar KY 160 genetically engineered to express a synthetic gene for tolerance to phenoxy herbicides.
[3]SAD2 - Cultivar KY 160 genetically engineered to express a modified version of the SAD1 synthetic gene for phenoxy herbicide tolerance.
[4]Pound of Active Ingredient per Acre Equivalent of 2,4-D (Isooctyl Ester Formulation).
[5]Dry Matter Yield expressed as grams/plant/replication/treatment

TABLE 2

Statistical Analysis of Yield Effects as Conditioned by Spray Rates on Transgenic and Non-transgenic Dark Fired Tobacco Genotype KY 160.

A) Analysis of Variance for Variable: Plant Yield

| Source | DF | Sum of Squares | Mean Square | F Value | Pr > F |
|---|---|---|---|---|---|
| Genotype | 2 | 1793.299 | 896.65 | 42.9 | 0.001* |
| Spray Rate | 2 | 155.033 | 77.52 | 3.71 | 0.033* |
| Geno × Spray | 4 | 200.113 | 50.03 | 2.39 | 0.066 |
| Error | 42 | 877.877 | 20.90 | | |

| R-Square | C.V. | Root MSE | Plant Yield Mean |
|---|---|---|---|
| 0.709 | 11.646 | 4.571 | 39.255 |

B) Analysis of Variance for Variable: Plant Corrected Yield

| Source | DF | Sum of Squares | Mean Square | F Value | Pr > F |
|---|---|---|---|---|---|
| Genotype | 2 | 1960.360 | 980.18 | 52.68 | 0.001* |
| Spray Rate | 2 | 149.550 | 74.78 | 4.02 | 0.025* |
| Geno × Spray | 4 | 245.748 | 61.44 | 3.30 | 0.019* |
| Error | 42 | 781.391 | 18.60 | | |

| R-Square | C.V. | Root MSE | Plant Corrected Yield Mean |
|---|---|---|---|
| 0.751 | 10.718 | 4.313 | 40.244 |

C) Analysis of Variance for Variable: Leaf Yield

| Source | DF | Sum of Squares | Mean Square | F Value | Pr > F |
|---|---|---|---|---|---|
| Genotype | 2 | 494.749 | 247.37 | 38.47 | 0.001* |
| Spray Rate | 2 | 92.513 | 46.26 | 7.19 | 0.021* |
| Geno × Spray | 4 | 74.535 | 18.63 | 2.90 | 0.033* |
| Error | 42 | 270.042 | 6.43 | | |

| R-Square | C.V. | Root MSE | Leaf Yield Mean |
|---|---|---|---|
| 0.710 | 16.952 | 2.535 | 14.958 |

D) Analysis of Variance for Variable: Corrected Leaf Yield

| Source | DF | Sum of Squares | Mean Square | F Value | Pr > F |
|---|---|---|---|---|---|
| Genotype | 2 | 564.432 | 282.22 | 50.93 | 0.001* |
| Spray Rate | 2 | 88.529 | 44.27 | 7.99 | 0.001* |
| Geno × Spray | 4 | 87.609 | 21.90 | 3.95 | 0.008* |
| Error | 42 | 232.747 | 5.54 | | |

| R-Square | C.V. | Root MSE | Plant Yield Mean |
|---|---|---|---|
| 0.761 | 14.762 | 2.354 | 15.946 |

E) Analysis of Variance for Variable: Percentage Leaf Yield

| Source | DF | Sum of Squares | Mean Square | F Value | Pr > F |
|---|---|---|---|---|---|
| Genotype | 2 | 0.347 | 0.0174 | 16.05 | 0.001* |
| Spray Rate | 2 | 0.009 | 0.0048 | 4.40 | 0.018* |
| Geno × Spray | 4 | 0.018 | 0.0046 | 4.24 | 0.006* |
| Error | 42 | 0.045 | 0.0011 | | |

| R-Square | C.V. | Root MSE | Plant Yield Mean |
|---|---|---|---|
| 0.579 | 8.423 | 0.033 | 0.390 |

Example 2

Increased Yield of Fruit as a Result of Application of 2,4-D to Transgenic Tomato Plants A. Experimental Design The use of exogenously supplied synthetic auxins on agronomic crops to elicit direct non-herbicidal effects was further assessed using genetically-engineered tomato plant lines expressing a synthetic auxin metabolizing gene, and non-genetically-engineered controls. Tomato was utilized to model fruit retention (fruit set) and fruit yield. The transgenic tomato line was utilized in the T2 generation with the transgene fixed in a homozygous fashion. The tomato genotype UC82L was utilized as the control, as well as the background for tranformation with the pPZP211-PNPT-311-SAD2 binary plasmid. This genotype was chosen because it is more likely to closely approximate the behavior of field-grown tomatoes than some short-life-cycle laboratory strains of tomato.

In the same manner as for tobacco, the research was conducted in a single phase entailing characterization of response variables when plants were subjected to the maximum (1×rate=1 pound/acre of active ingredient) and low (¼×=4 ounces/acre of active ingredient) rates of exogenously applied 2,4-D. The overall experimental design was comprised of three parallel completely randomized designs with spray rate and genotype as the main factors. Three replications were performed for each treatment within each experiment. Each replication was the average of three plants that were harvested over a period of 60 days. Fruit number, fruit weight and flower number were measured directly, with average fruit weight and average fruit per plant being derived by dividing fruit weight and fruit number within a replication by the number of plants (3). Tomato fruit yield was measured on fresh fruit and recorded in grams.

B. Transformation of Tomato to Produce Genetically-Engineered Lines

The binary plasmid pPZP211-PNPT-311-SAD2 used for transformation was the same as that used in Example 1, and tomato (*Lycopersicon esculentum*) cultivar UC82B (a cultivar nearly identical to UC82L) was transformed by *Agrobacterium*-mediated transformation of leaf tissue with the binary plasmid as described in Example 1. Transgenic plants were produced from the transformed leaf tissue as described in Example 1.

C. Yield Assays

Non-transgenic and transgenic seed were germinated and grown as described in Example 1 for tobacco. The transgenic tomato line was utilized in the T2 generation with the transgene fixed in a homozygous fashion.

The plants with 4 fully-extended leaves retained were sprayed as described in Example 1. Each replication (3 plants) was sprayed independently and permitted to dry before being moved back to the greenhouse for further growth for 60 days.

Fruit number, fruit weight, and flower number were measured directly during this 60-day period. Tomato fruit yield was measured on fresh fruit and recorded in grams.

D. Results

The results are presented in the following tables. The analyses of variance for tomato fruit response variables (Table 3) shows that significant differences were found in total fruit yield, total flower number, and average fruit weight between treatments. Genotype was determined to be the significant factor for total fruit yield, which, just as for the tobacco model above, was expected, since non-transgenic material that is susceptible to a herbicide should display reduced vigor when treated with that herbicide. What was not expected, but is evident in Table 4, was the increase in total yield of the transgenic lines expressing the herbicide tolerance gene. Total flower number was also determined to be significantly different between treatments, but evaluation of fruit per plant (a later measure influenced by flower number) did not show any significant differences between treatments. This left average fruit weight as the final remaining significant measure affected by the treatments. In the case of average fruit weight, genotype by spray rate interactions were significant, as can be seen from Table 3. When the means of the measured traits are compared (Table 4), it is clear that the ¼× rate of 2,4-D application resulted in an increase in average fruit weight for both control and transgenic lines. This increase is most striking in the non-transgenic material, although evident also in transgenic material. The ¼× rate also affected total flower number, reducing the number of flowers in the control material and increasing the number of flowers in the transgenic lines.

In summary, the fruit yield data demonstrated that there was a positive benefit in transgenic lines treated with a phenoxy herbicide. This again reveals a new and novel use of these herbicides in combination with genes conditioning tolerance to them for providing demonstrable yield increases. The commercialization of tomato or other fruit crops expressing genes for tolerance to phenoxy herbicides would permit growers to obtain yield increases in crops normally susceptible to these same herbicides.

In combination, the results of Examples 1 and 2 show that 2,4-D metabolizing genes provide tolerance to 2,4-D in both tobacco and tomato and, in combination with application of phenoxy herbicide, give yield increases. The efficacy of these genes in two distinctly different crops also demonstrates the potential for use in other crops to increase forage yield (such as alfalfa) or fruit yield (such as melons). Not only will transgenic crops expressing these genes benefit from potential increases in yield, these transgenic crops will be applied to capitalize on the benefits of weed control provided by phenoxy herbicides.

TABLE 3

Statistical Analysis of Tomato Yield Components As Influenced by Genotype and Spray Rate A) Analysis of Variance for Variable: Tomato Total Fruit Yield

| Source | DF | Sum of Squares | Mean Square | F Value | Pr > F |
|---|---|---|---|---|---|
| Genotype | 1 | 14402.401 | 14402.401 | 6.91 | 0.025* |
| Spray Rate | 2 | 312.938 | 156.469 | 0.08 | 0.928 |
| Geno × Spray | 2 | 4404.824 | 2202.412 | 1.06 | 0.383 |
| Error | 10 | 20852.384 | 2085.238 | | |

| R-Square | C.V. | Root MSE | Total Fruit Yield Mean |
|---|---|---|---|
| 0.478 | 51.423 | 45.66 | 88.800 |

B) Analysis of Variance for Variable: Total Tomato Fruit Number

| Source | DF | Sum of Squares | Mean Square | F Value | Pr > F |
|---|---|---|---|---|---|
| Genotype | 1 | 49.000 | 49.000 | 3.47 | 0.092 |
| Spray Rate | 2 | 34.241 | 17.121 | 1.21 | 0.337 |
| Geno × Spray | 2 | 65.592 | 32.796 | 2.32 | 0.148 |
| Error | 10 | 141.167 | 14.117 | | |

TABLE 3-continued

Statistical Analysis of Tomato Yield Components As Influenced by Genotype and Spray Rate

| R-Square | C.V. | Root MSE | Total Fruit Mean |
|---|---|---|---|
| 0.513 | 53.67 | 3.76 | 7.000 |

C) Analysis of Variance for Variable: Total Flower Number

| Source | DF | Sum of Squares | Mean Square | F Value | Pr > F |
|---|---|---|---|---|---|
| Genotype | 1 | 100.000 | 100.000 | 1.69 | 0.222 |
| Spray Rate | 2 | 376.119 | 188.059 | 3.19 | 0.085 |
| Geno × Spray | 2 | 471.637 | 235.815 | 4.00 | 0.053* |
| Error | 10 | 590.000 | 50.00 | | |

| R-Square | C.V. | Root MSE | Total Flower Mean |
|---|---|---|---|
| 0.616 | 49.95 | 7.68 | 15.375 |

D) Analysis of Variance for Variable: Average Fruit Weight

| Source | DF | Sum of Squares | Mean Square | F Value | Pr > F |
|---|---|---|---|---|---|
| Genotype | 1 | 4.378 | 4.378 | 0.35 | 0.566 |
| Spray Rate | 2 | 223.890 | 111.945 | 9.02 | 0.058 |
| Geno × Spray | 2 | 172.352 | 86.176 | 6.940 | 0.013* |
| Error | 10 | 124.107 | 12.410 | | |

| R-Square | C.V. | Root MSE | Plant Yield Mean |
|---|---|---|---|
| 0.763 | 24.67 | 3.52 | 14.281 |

E) Analysis of Variance for Variable: Average Fruit Per Plant

| Source | DF | Sum of Squares | Mean Square | F Value | Pr > F |
|---|---|---|---|---|---|
| Genotype | 1 | 3.063 | 3.063 | 3.47 | 0.092 |
| Spray Rate | 2 | 2.140 | 1.070 | 1.21 | 0.337 |
| Geno × Spray | 2 | 4.099 | 2.049 | 2.32 | 0.148 |
| Error | 10 | 8.822 | 0.822 | | |

| R-Square | C.V. | Root MSE | Average Fruit/Plant Mean |
|---|---|---|---|
| 0.513 | 53.67 | 0.94 | 1.750 |

TABLE 4

Genotype by Spray Rate Interaction Means for Response Variables

| Genotype | Spray Rate[3] | Total Yield[4] | Total[5] Fruit No. | Fruit per[6] Plant | Total[7] Flowers | Fruit[8] Weight |
|---|---|---|---|---|---|---|
| UC82L[1] | 0 | 77.4 | 9.7 | 2.4 | 26.0 | 8.0 |
| UC82L | 1/4X | 66.1 | 3.0 | 0.8 | 6.0 | 26.0 |
| UC82L | 1X | 35.3 | 2.3 | 0.6 | 4.3 | 14.1 |
| SAD2[2] | 0 | 92.9 | 7.5 | 1.9 | 16.0 | 12.9 |
| SAD2 | 1/4X | 122.9 | 8.7 | 2.2 | 17.3 | 14.4 |
| SAD2 | 1X | 131.9 | 9.7 | 2.4 | 19.7 | 13.7 |

[1]UC82L - Commercially grown cultivar of canning tomato used by industry for paste/catsup
[2]SAD2 - Cultivar UC82B, nearly identical to above cultivar UC82L, genetically engineered to express a synthetic gene for tolerance to phenoxy herbicides
[3]Pounds of Active Ingredient per Acre Equivalent of 2,4-D (Isooctyl Ester Formulation)
[4]Fresh Fruit Yield expressed as grams/plant/replication/treatment
[5]Total Fruit Number/replication/treatment
[6]Fruit Number/plant/replication/treatment
[7]Flower Number/replication/treatment
[8]Average Fresh Fruit Weight expressed as grams/fruit/plant/replication/treatment

Example 3

Increased Yields by Application of 2,4-D to Transgenic Cotton Plants

Transgenic cotton plants (transformed as described in Bayley et al., *Theor. Appl. Genet.*, 83:645-649 (1992)) were grown from transgenic seed obtained from USDA, Lubbock, Tex. The cotton plants were sprayed with 2,4-D amine at 1 lb of active ingredient per acre. It was found that the 2,4-D amine application significantly increased the yield of cotton. The results are presented in Table 5 below.

TABLE 5

| COTTON LINE[1] | HERBICIDE RATE | SEED COTTON YIELD[2] | PERCENT INCREASE |
|---|---|---|---|
| X-2600 | 0 | 1986 | — |
| X-2600 | 1 lb/acre | 2145 | 8.0 |
| X-2603 | 0 | 2597 | — |
| X-2603 | 1 lb/acre | 2790 | 7.4 |
| X-2606 | 0 | 2566 | — |
| X-2606 | 1 lb/acre | 3067 | 19.5 |
| X-2609 | 0 | 2327 | — |
| X-2609 | 1 lb/acre | 2301 | −1.1 |
| X-2614 | 0 | 1991 | — |
| X-2614 | 1 lb/acre | 2660 | 33.6 |
| X-2615 | 0 | 2065 | — |
| X-2615 | 1 lb/acre | 2380 | 15.3 |
| X-2619 | 0 | 2056 | — |
| X-2619 | 1 lb/acre | 2235 | 8.7 |
| AVERAGE | | | 13.0 |

[1] All transformed with tfdA gene.
[2] Pounds/acre; average of 4 replications.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

---

We claim:

1. A method of improving the yield of a crop comprising:
growing transgenic plants comprising heterologous DNA selected from the group consisting of SEQ ID NO:2 and SEQ ID NO:3 to produce a crop, the transgenic plants being able to metabolize at least one synthetic auxin;
applying a synthetic auxin to the plants at least once during their growth, the synthetic auxin being one that can be metabolized by the transgenic plants; and
harvesting the crop.

2. The method of claim 1 wherein the transgenic plants are annuals.

3. The method of claim 1 wherein the transgenic plants are dicotyledonous plants.

4. The method of claim 1 wherein the transgenic plants are tomato plants.

5. The method of claim 1 wherein the transgenic plants are tobacco plants.

6. The method of claim 1 wherein the transgenic plants are cotton plants.

7. The method of any one of claims 1-6 wherein the transgenic plants are able to metabolize at least one phenoxy auxin.

8. The method of claim 7 wherein the transgenic plants are able to metabolize a phenoxy auxin selected from the group consisting of 2,4-dichlorophenoxy acetic acid, 2,4-dichlorophenoxy butyric acid, and esters of either of them.

9. The method of any one of claims 1-6 wherein the auxin applied to the plants is a phenoxy auxin.

10. The method of claim 9 wherein the auxin applied to the transgenic plants is a phenoxy auxin selected from the group consisting of 2,4-dichlorophenoxy acetic acid, 2,4-dichlorophenoxy butyric acid, and esters of either of them.

11. The method of claim 7 wherein the auxin applied to the transgenic plants is a phenoxy auxin.

12. The method of claim 11 wherein the auxin applied to the transgenic plants is a phenoxy auxin selected from the group consisting of 2,4-dichlorophenoxy acetic acid, 2,4-dichlorophenoxy butyric acid, and esters of either of them.

13. The method of claim 8 wherein the auxin applied to the transgenic plants is a phenoxy auxin selected from the group consisting of 2,4-dichlorophenoxy acetic acid, 2,4-dichlorophenoxy butyric acid, and esters of either of them.

* * * * *